(12) United States Patent
Parente

(10) Patent No.: US 9,151,747 B1
(45) Date of Patent: Oct. 6, 2015

(54) SUCRALOSE ANTIBODY AND IMMUNOASSAY

(71) Applicant: Amy D. Parente, Erie, PA (US)

(72) Inventor: Amy D. Parente, Erie, PA (US)

(73) Assignee: Mercyhurst University, Erie, PA (US)

( * ) Notice: Subject to any disclaimer, the term of this patent is extended or adjusted under 35 U.S.C. 154(b) by 37 days.

(21) Appl. No.: 14/209,467

(22) Filed: Mar. 13, 2014

Related U.S. Application Data

(60) Provisional application No. 61/784,747, filed on Mar. 14, 2013.

(51) Int. Cl.
*G01N 33/543* (2006.01)

(52) U.S. Cl.
CPC .................................. *G01N 33/543* (2013.01)

(58) Field of Classification Search
None
See application file for complete search history.

(56) References Cited

U.S. PATENT DOCUMENTS

| | | | |
|---|---|---|---|
| 4,376,110 A | 3/1983 | David et al. | 436/513 |
| 5,498,709 A | 3/1996 | Navia et al. | 536/124 |
| 7,749,772 B1 | 7/2010 | Wang | 36/514 |

OTHER PUBLICATIONS

S.W. Mann et al., "A Combined Chronic Toxicity/Carcinogenicity Study of Sucralose in Sprague-Dawley Rats", Food and Chemical Toxicology, 2000, 19 pages.
H.C. Grice et al., "Sucralose—An overview of the Toxicity Data", Food and Chemical Toxicology, 2000, 6 pages.
A. Roberts et al., "Sucralose Metabolism and Pharmacokinetics in Man", Food and Chemical Toxicology, 2000, 11 pages.
M. Hewetson et al., "Sucrose Concentration in Blood: A New Method for Assessment of Gastric Permeability in Horses with Gastric Ulceration", J Vet Intern Med, 2006, 7 pages.
Wenlong Qiu et al., "GC-MS Determination of Sucralose in Splenda", Chromatographia, 2007, 5 pages.
Naomi Lubick, "Artificial sweetener persists in the environment", Environmental Science & Technology, 2008, 1 page.
Naomi Lubick, "Artificial sweetener makes ideal tracer", Environmental Science & Technology, 2009, 1 page.
Robert Loos et al., Sucralose screening in European surface waters using a solid-phase extraction-liquid chromatography-triple quadrupole mass spectrometry method, Journal of Chromatography A, 2009, 6 pages.
Ralph Mead et al., "Occurrence of the artificial sweetener sucralose in coastal and marine waters of the United States", Marine Chemistry, 2009, 5 pages.
Juliane Hollender et al., Elimination of Organic Micropollutants in a Municipal Wastewater Treatment Plant Upgraded with a Full-Scale Post-Ozonation Followed by Sand Filtration, Environ. Sci. Technol., 2009, 8 pages.
Arnold Bahlmann et al., "Monitoring carbamazepine in surface and wastewaters by an immunoassay based on a monoclonal antibody", Anal Bioanal Chem, 2009, 12 pages.
"Fluoxetine Elisa Kit Instructions", Neogen Corporation, 2010, 5 pages.
Imma Ferrer et al., "Analysis of sucralose and other sweeteners in water and beverage samples by liquid chromatography/time-of-flight mass spectrometry", Journal of Chromatography A, 2010, 8 pages.
Lindsay Soh et al., "Fate of Sucralose through Environmental and Water Treatment Processes and Impact on Plant Indicator Species", Environmental Science &Technology, 2011, 7 pages.
Douglas Mawhinney et al., "Artificial Sweetener Sucralose in U.S. Drinking Water Systems", Environmental Science & Technology, 2011, 7 pages.
Johanna Minten et al., "A method for the analysis of sucralose with electrospray LC/MS in recipient waters and in sewage effluent subjected to tertiary treatment technologies", Intern. J. Environ. Anal. Chem., 2011, 11 pages.
Cesar Torres et al., "Fate of Sucralose During Wastewater Treatment", Environmental Engineering Science, 2011, 7 pages.
Wiklund et al., "Sucralose—An ecotoxicological challenger?", Chemosphere, 2011, 6 pages.
G. Kohler et al., Continuous cultures of fused cells secreting antibody of predefined specificity, 1975, 3 pages.

*Primary Examiner* — Jacob Cheu
(74) *Attorney, Agent, or Firm* — Robert M. Bauer

(57) ABSTRACT

Kits and methods detect sucralose or determine sucralose concentration in a sample by using polyclonal or monoclonal anti-sucralose antibodies. An ELISA assay or other immunoassay detects sucralose or determines sucralose concentration in various samples.

10 Claims, 4 Drawing Sheets

SUCRALOSE ANTIBODY AND IMMUNOASSAY

This application claims the priority benefit of the filing date of U.S. Provisional Patent Application No. 61/784,747 filed on Mar. 14, 2013, which provisional application is hereby incorporated by reference in its entirety.

FIELD OF THE INVENTION

This invention relates generally to antibodies and the uses therefore. More specifically, this invention provides anti-sucralose antibodies and methods of using the same.

BACKGROUND

Sucralose is a chlorinated molecule resembling table sugar, as evidenced in FIG. 1. Sucralose is 600 times sweeter than table sugar and undergoes minimal breakdown by the human body. This allows users to sweeten their food and drink without any additional calories. Because sucralose is a chlorinated molecule, it may have harmful effects on humans and animals. Sucralose toxicity is a largely unstudied and unquantified field. In addition to studying sucralose's possible toxicity, sucralose can be studied because it is a good marker for wastewater movement and presence. Thus, accurate, cost-effective detection of sucralose is important because it will better allow researchers to understand the molecule's effect on varying ecosystems, as well as monitor the flow of wastewater through water systems. Currently, there is no accurate method of sucralose detection that is inexpensive, portable, or does not require significant sample preparation.

Two of the more common methods of sucralose detection are liquid chromatography with mass spectrometry (LC-MS), and gas chromatography with mass spectrometry (GC-MS). Because sucralose is hydrophilic, samples must be prepared before analysis by GC-MS. While GC-MS has high selectivity and sensitivity, the preparation required to use GC-MS makes it less than ideal for sucralose detection.

While LC-MS does not require the same sample preparation as GC-MS, the equipment associated with LC-MS can be expensive and cost prohibitive. Additionally, LC-MS, like GC-MS, requires large pieces of equipment that cannot be carried into the field. Rather, the conventional techniques require researchers to obtain samples in the field and transport them to a laboratory for analysis. This delay in time prevents researchers from being able to adjust their sample collection in the field based on findings of high or low sucralose.

BRIEF SUMMARY

In one preferred embodiment, polyclonal and monoclonal anti-sucralose antibodies are provided. In another preferred embodiment, there are provided kits and methods for sucralose detection, which involves sucralose selective antibodies and immunoassays to detect or quantify sucralose in a sample. By developing monospecific polyclonal or monoclonal anti-sucralose antibodies, an accurate immunoassay, such as an ELISA assay, can be developed to detect sucralose in various samples. The ELISA assay can be taken into the field, allowing researchers to obtain results quickly while in the field when used in conjunction with a portable detector, such as an infrared or fluorescence detector. In another preferred embodiment, the anti-sucralose antibodies can be used in a lateral flow immunoassay, which can determine presence of sucralose. Researchers can thus obtain immediate, reliable data from the field for a small cost relative to GC-MS and HPLC. Such embodiments are advantageous because they eliminate the preparation time and costs associated with traditional sucralose measurement techniques.

DETAILED DESCRIPTION OF THE PREFERRED EMBODIMENTS

Figure 1:
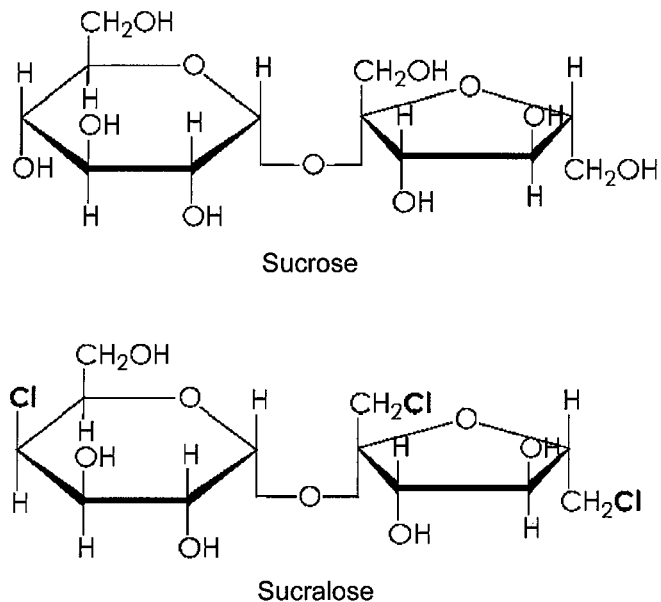
FIG. 1 depicts the chemical structure of sucrose and sucralose.

Throughout this application, various references or publications are cited. Disclosures of these references or publications in their entireties are hereby incorporated by reference into this application in order to more fully describe the state of the art to which this invention pertains. Applicant's previous publication—*Immunological Detection Method for the Artifical Sweetener Sucralose in the Environment*, Frederickson and Diegelman-Parente, *The Journal of Mercyhurst Chemistry and Biochemistry*, Vol. 1, No. 2, May 2, 2012, enclosed in the provisional patent application and also incorporated herein by reference, may be consulted in order to make clear applicant's invention.

Antibodies are proteins that bind to specific molecules called antigens, and are used by an organism to fight off disease. When a foreign object, such as a virus or bacteria is introduced into the body, the B cells in the body produce antibodies that can recognize the foreign object to fight off the foreign object. While antibodies are usually produced in response to a disease, antibodies can also be made in animals by manipulating the immune system and forcing the immune system to produce antibodies that would recognize the desired antigen.

The term "antibody" as used herein refer broadly to any immunological binding agent or molecule that comprises an antigen binding domain, including polyclonal and monoclonal antibodies. Depending on the type of constant domain in the heavy chains, whole antibodies are assigned to one of five major classes: IgA, IgD, IgE, IgG, and IgM. Several of these are further divided into subclasses or isotypes, such as IgG1, IgG2, IgG3, IgG4, and the like. The subunit structures and three dimensional configurations of different classes of antibody are well known.

As will be understood by those in the art, the immunological binding reagents encompassed by the term "antibody" extend to all antibodies and antigen binding fragments thereof, including whole antibodies, dimeric, trimeric and multimeric antibodies; bispecific antibodies; chimeric antibodies; recombinant and engineered antibodies, and fragments thereof.

The term "antibody" is thus used to refer to any antibody-like molecule that has an antigen binding region, and this term includes antibody fragments that comprise an antigen binding domain such as Fab', Fab, F(ab')$_2$, single domain antibodies (DABs), T and Abs dimer, Fv, scFv (single chain Fv), dsFv, ds-scFv, Fd, linear antibodies, minibodies, diabodies, bispecific antibody fragments and the like.

The techniques for preparing and using various antibody-based constructs and fragments are well known in the art (see Kabat et al., 1991). Diabodies, in particular, are further described in EP 404,097 and WO 93/11161; whereas linear antibodies are further described in Zapata et al. (1995).

Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, Fv, dsFv, Fd, dAbs, T and Abs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments.

The antibodies or antibody fragments can be produced naturally or can be wholly or partially synthetically produced. Thus the antibody may be from any appropriate source, for example recombinant sources and/or produced in transgenic animals or transgenic plants. Thus, the antibody molecules can be produced in vitro or in vivo.

Figure 5:
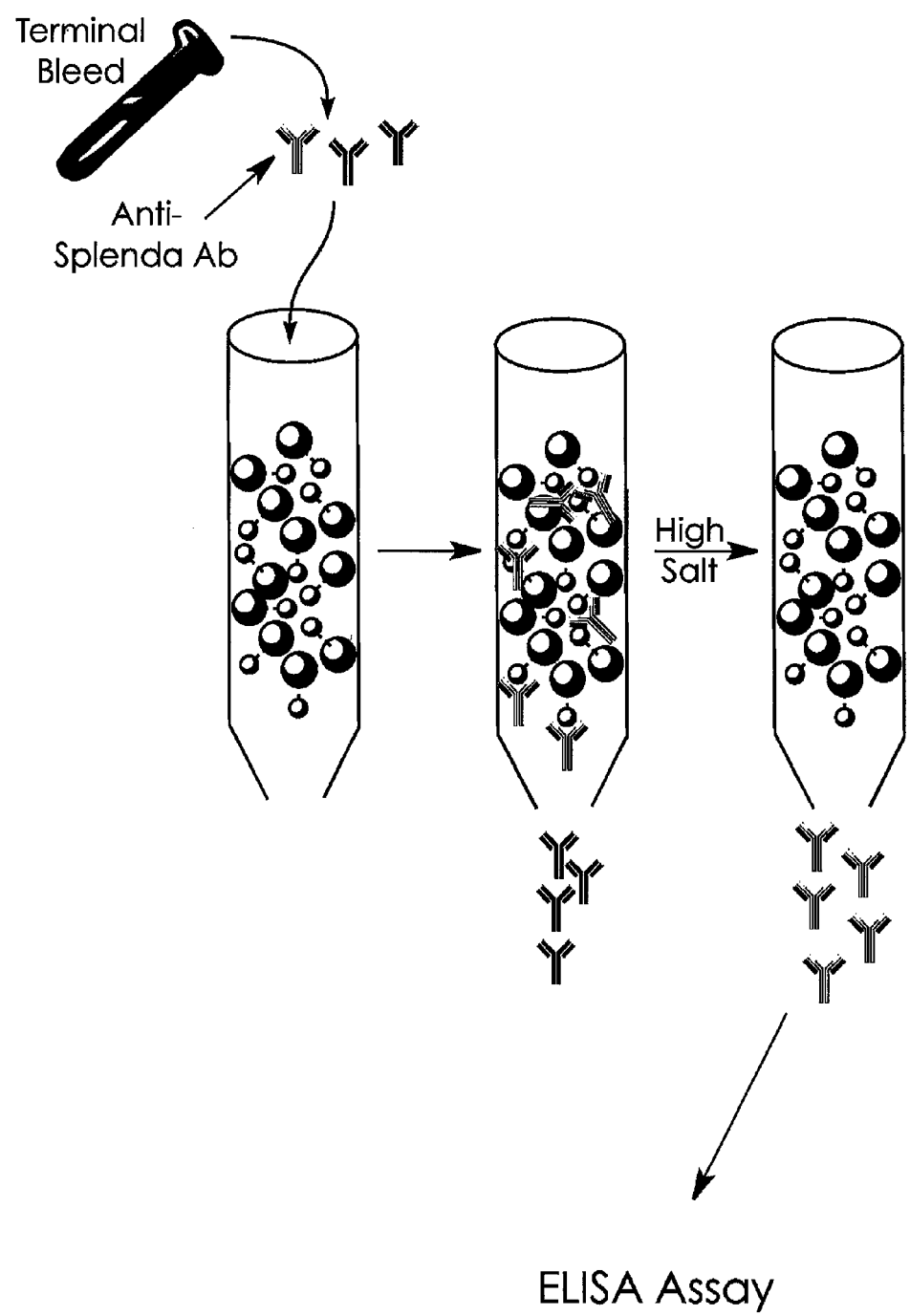
FIG. 5 depicts one preferred embodiment of a fast protein liquid chromatography.

In one preferred embodiment, the antibodies described herein involve rabbits, but antibodies may be synthesized or expressed in cells of any organism, including but not limited to bacteria, yeast, plant, insect, and animal. Once the antibodies are produced by the rabbits, the antibodies are purified using fast protein liquid chromatography (FPLC) and an antibody-specific resin, as depicted in FIG. 5. However, any variety of purification methods can be used, including, but not limited to, electrophoretic, molecular, immunological, and chromatographic techniques, including ion exchange, hydrophobic, affinity, and reverse-phase HPLC. The sucralose antibodies can be screened for functionality using a variety of techniques generally known in the art, including immunoassays, ELISAs, flow cytometry, immunodiffuision precipitation assays, and the like.

As it is generally known in the art, immunoassays are detection methods that result from the use of antibodies. One example of an immunoassay is an ELISA assay, which can measure concentrations of a target antigen in a sample. Another example is lateral flow immunoassay, which allows for the detection of antigen in a sample, but does not provide an accurate concentration. While immunoassays and the development of such assays from an antibody are well known in the art, researchers seeking to develop a new immunoassay are often constrained if the molecule they seek to detect does not have a compatible antibody. Such was the problem with sucralose, there was no compatible antibody for use in an immunoassay.

Monospecific Polyclonal Antibody Production, Detection, and Purification

Figure 2:
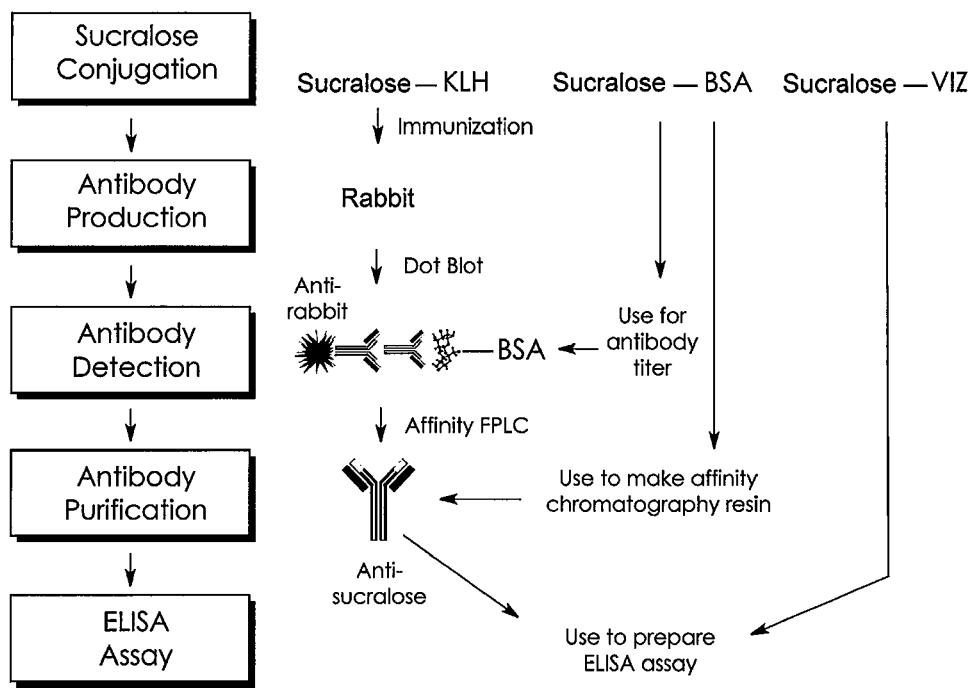
FIG. 2 depicts an overview of the antibody and assay creation system.

As discussed above, it is generally known in the art that monospecific polyclonal antibodies can be obtained using a variety of immunochemistry techniques. In one embodiment, FIG. 2 is a pictorial representation of the process of creating sucralose antibodies, but one of ordinary skill in the art would readily use any other technique or variation on this technique to produce monospecific polyclonal antibodies that bind to sucralose.

Sucralose Conjugation

Methods of conjugation are well-known in the art. In one embodiment, sucralose is conjugated to three different proteins or molecules: (1) keyhole limpet hemocyanin (KLH); (2) bovine serum albumin (BSA); and (3) a visible reporter protein or molecule (VIZ). This conjugation chemistry was accomplished using the chemical linker carbonyldiimidazole (CDI). Reactive hydroxyl groups (found on surface amino acids or carbohydrates of the proteins, or on sucralose itself) serve as nucleophiles, reacting with the electrophilic carbonyl group of CDI, displacing the imidazole leaving group of CDI.

Antibody Production

In one preferred embodiment, two rabbits were immunized via an intradermal (ID) route with the KLH-conjugate on Day 0 after a pre-bleed sample was taken 4 days prior. The volume may be, for example, 0.5 ml. The rabbits received booster injections of KLH-conjugate via intradermal (ID) route on day 7 and via subcutaneous (SC) route on days 14 and 28. On day 38, a 5 mL test bleed was drawn to determine if antibody was present and of sufficient quantity.

Antibody and Crude Protein Detection

A baseline level of antibody levels was determined before immunization from the pre-bleed sample using a standard titer assay. After immunization, quantitative detection of sucralose antibodies was performed using a sandwich ELISA assay using BSA-conjugate coated 96 well plates and an anti-rabbit primary antibody conjugated with horseradish peroxidase (HRP), which serves as a secondary antibody to the rabbit antibodies. Only antibodies specific for sucralose bound to the BSA-conjugate and thus only these rabbit-produced proteins were detected by the addition of the secondary antibody.

Figure 3:
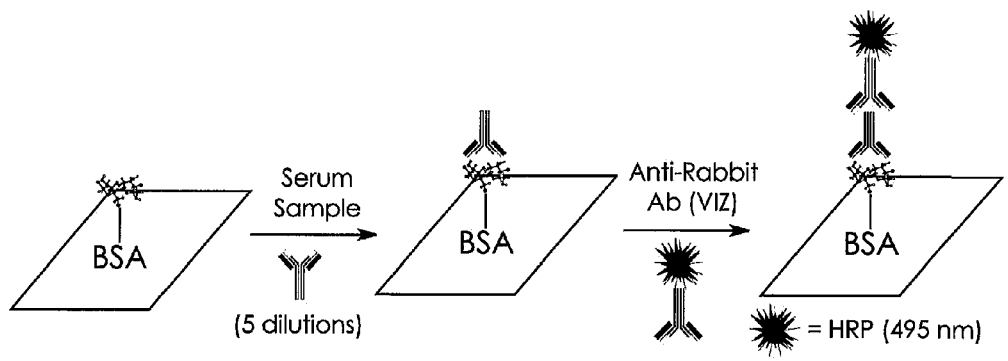
FIG. 3 depicts one method of determining antibody titer of a test bleed according to a preferred embodiment of the invention.

Antibody titer was determined by comparing the level of antibody in a pre-bleed sample (before rabbits were injected with the KLH-conjugate) to various dilutions of test bleed samples collected at 38 days post injection. Antibody titer is determined to verify the antibodies produced were sucralose specific. As it is generally known in the art, the assay involves coating a plate with BSA-conjugated sucralose, introducing a series of dilutions of the antibodies from the rabbits, washing unbound rabbit antibodies and introducing a secondary antibody, as represented in FIG. 3. The larger the titer level, the higher the concentration of antibody produced. In general, levels in the 5,000 range indicate a positive, but lagging, antibody production. In one experiment, the titer levels from both rabbits were greater than 20,000, indicative of a very strong antigenic response. One of the rabbits showed a titer level as high as 62,500.

Qualitative detection of total antibody was determined with an SDS-PAGE using a blue triphenylmethane stain on the same pre-bleed and test bleed samples used in the titer assay. The predominant proteins were approximately 50 kDa and 25 kDa in molecular weight, which is consistent with the expected molecular weights of the heavy and light chains for IgG antibodies of 55 kDa and 25-27 kDa. MGH, which is a fusion protein of green fluorescent protein (GFP) and malate dehydrogenase (MDH), was used as a comparison protein in the SDS-PAGE because it is of similar molecular weight (65 kDa), but not of rabbit origin.

Figure 4:
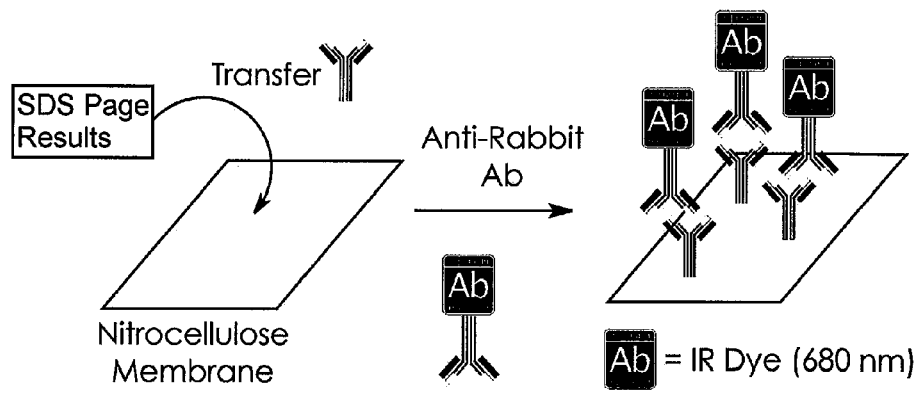
FIG. 4 depicts one preferred embodiment of a Western blot on the test bleed.

Antibodies separated by SDS-PAGE were then transferred to a nitrocellulose membrane and probed by goat anti-rabbit antibodies conjugated with an IR dye (IRDye 680LT ($\lambda$=680 nm)) in a Western blot, as represented in FIG. 4. The predominant proteins were again of molecular weights consistent with the expected molecular weights of the heavy and light chains for IgG antibodies. MGH was again used as a negative control for the secondary antibody, the anti-rabbit antibody conjugated to HRP.

Antibody Purification

Anti-sucralose antibodies were purified from serum using fast protein liquid chromatography (FPLC) and an antibody-specific resin. After initial loading and washing of the column using a phosphate-buffered saline solution, a salt gradient was used to elute the protein. Non-antibody proteins, which comprise the majority of the mixture, were eluted very early, while anti-sucralose antibodies were not eluted until the addition of a salt gradient.

The following is the buffer and program conditions. Running buffer: 10 mM sodium phosphate, pH 7.5, 100 mM NaCl, 1 mM PMSF. Elution buffer: same as running buffer, but 500 mM NaCl. FPLC program: flow rate=1 ml/min, 3 mL fractions collected, total program time=270 minutes. Step 1=75 minutes, 100% running buffer. Step 2=195 minutes, 0-100% gradient of elution buffer. A Bradford assay was used to identify fractions with protein detection using a microplate reader. Antibody and crude protein detection were determined as described above.

In addition, crude protein and total antibody were probed using SDS-PAGE and Western blot, respectively. As FPLC separated antibodies from total protein, antibody was detected by Western blot. This more sensitive method is necessary as antibodies represent only a small fraction of the total protein present in the serum sample.

Monoclonal Antibody Production

Unlike polyclonal antibodies, monoclonal antibodies are identical to one another in every way. Monoclonal antibodies are a preferred embodiment of sucralose specific antibodies. In one embodiment, the monoclonal antibodies are produced from a hybridoma, a process well known in the art and first described by Milstein and Köhler, *Nature*, Vol. 256 495-497, 1975. Once an organism is properly immunized against sucralose, one having ordinary skill in the art can produce anti-sucralose monoclonal antibody using standard techniques in the art. Producing the monoclonal antibody involves harvesting the spleen of a laboratory animal that has been immunized against sucralose (for example, a mouse). The B-cells from the harvested spleen cells are isolated into single cells and fused with immortal myeloma cells to form hybridoma cells. The hybridoma cells produce the antibodies of the B-cell yet have the infinite longevity of the immortal myeloma cells.

Another technique available to one skilled in the art is recombinant monoclonal antibodies. This technique involves extracting the messenger RNA (mRNA) from the hybridoma or laboratory animal spleen cells and creating the mRNA's complementary DNA (cDNA). The antibody cDNA can then be amplified using heavy or light chain primers by PCR. Creating recombinant DNA allows one skilled in the art to manipulate the production of monoclonal antibodies by controlling various factors such as rate of gene expression and type of host cell.

Assay Development

Figure 6:
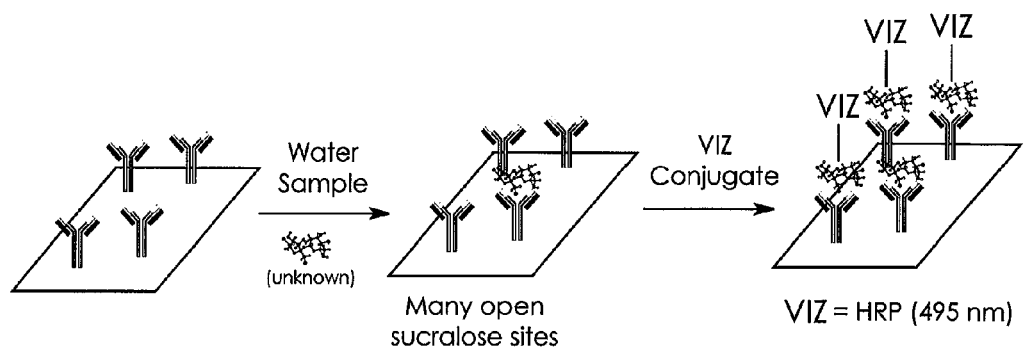
FIG. 6 depicts one preferred embodiment of a competitive ELISA assay.

One of ordinary skill in the art would readily recognize that several immunoassays can be developed from the antibodies described herein. The first is an ELISA assay, of which there are several embodiments. In the first embodiment, a competitive ELISA assay, represented by FIG. 6, monospecific polyclonal or monoclonal anti-sucralose antibodies are attached to the base of the well in a well plate. Typically, the well plate contains 96 wells. Each of the wells has a different number of antibodies so that the well plate creates an antibody distribution gradient. The sample is introduced into the wells and any sucralose in the sample will bind with the antibodies in the wells. Once the sucralose has had time to bind, the sample is washed from the wells and sucralose conjugated to a marker or tag would be introduced into the wells. Any antibodies which do not have sucralose bound to them from the sample will bind with the sucralose conjugated to a marker. A detector compatible with the marker then determines how much of the conjugated sucralose is bound to the antibodies. In this variation, there is an inverse relationship because the more markers that are present in the wells, the less sucralose is in the sample because the conjugated sucralose has little competition from the sample.

In another variation, also known as a "sandwich ELISA," the monospecific polyclonal or monoclonal anti-sucralose antibodies would again be attached to the base of the wells in a well plate. Then, the sample would be introduced and the sucralose in the sample would be given time to bind to the antibodies. The sample would be washed from the wells and a second set of antibodies conjugated to a marker would be introduced into the wells. The second set of antibodies would create a "sandwich" with the sucralose because the sucralose would bind to the antibodies attached to the wells and the conjugated antibodies would bind to the sucralose. The proper detector for the marker conjugated to the second set of antibodies can then be used to determine the concentration. Unlike the previous method, the more markers that are detected, the higher the sucralose concentration in the sample.

Another possible immunoassay is a lateral flow immunoassay. In one embodiment, a lateral flow immunoassay involves a strip of substrate where the sample moves along the strip using capillary action. Once the sample reaches the point of the strip where the antibodies are located, there will be a reaction when the sucralose binds with the antibodies. If the antibodies are configured similar to a sandwich ELISA assay, then the strip will change colors. While a lateral flow immunoassay strip will not give a quantitative measure of sucralose in the sample, it would be beneficial for researchers who can quickly determine whether sucralose is in the sample before using the time and resources to run a quantitative analysis.

Assay Development Methods

The method for developing an immunoassay from an antibody is well known in the art. Once the antibody is developed, the immunoassay can be created by a commercial kit or by contracting with a third-party whose business involves the creation of an immunoassay. As an illustrative example, a well plate can be coated with antibodies by diluting the anti-sucralose antibodies described herein with phosphate buffered saline (PBS). The antibody-PBS solution is then added to the wells, covered, and incubated overnight. The wells are then washed with a wash buffer, such as PBS with polysorbate 20. The wells should then be blocked by using a blocking buffer, such as PBS with polysorbate 20 and BSA. Lastly, the plates are incubated and then washed four times using the PBS with polysorbate 20 solution.

In one embodiment, the present invention provides an isolated polyclonal or monoclonal antibody that binds to sucralose. In one embodiment, the antibody is produced by a hybridoma or by recombinant methods.

The present invention also provides a host cell expressing the above antibody.

The present invention also provides an immunoassay for detecting the presence of sucralose in a sample, comprising the steps of: contacting the sample with the antibody described herein, thereby forming immune complexes between the antibody and sucralose; and detecting and relating the binding of the antibody to the sucralose to the presence of the sucralose in the sample. In one embodiment, the antibody in this assay is labeled.

The present invention also provides a lateral flow immunoassay strip for detecting the presence of sucralose in a fluid sample, comprising a membrane strip coated with a sucralose-protein conjugate on a test line, and particles coated with the antibody described herein.

The present invention also provides a method for detecting the presence of sucralose in a sample, comprising the steps of: obtaining a sample; contacting a lateral flow immunoassay strip (such as the one described above) with the sample; allowing the sample to migrate along the strip; and determining whether the immunoassay is positive or negative for the presence of sucralose in the sample by detecting the presence or absence of the antibody-coated particles in a test line region of the lateral flow immunoassay.

Lateral flow assays can operate using a derived antibody to target analyte in both a sandwich immunoassay (paragraph 0035) or competition immunoassay (paragraph 0034) format. In either format, the lateral flow immunoassay generally has three compartments—the sample pad, conjugate pad, and test pad. This system can be used to accommodate the use of derived antibodies in both sandwich-type and competition-type immunoassays. In either type, the sample solution (i.e. a solution with an unknown level of sucralose) is first soaked into the sample pad. This solution then flows into the conjugate pad that has reagents necessary to facilitate detection of the desired analyte (sucralose in the preferred embodiments). The main difference between the sandwich-type and competition-type lateral flow immunoassay is which substance(s) the sample solution comes in contact with in the conjugate pad.

In the sandwich immunoassay, the sample solution encounters analyte-specific antibodies and reagents necessary to facilitate the interaction of these antibodies with their target analyte (in the preferred embodiments, this would include salts, anti-sucralose antibodies which are either dye-tagged or conjugated to another enzyme capable of performing dye-generating chemistry). At this point, while sucralose will bind to anti-sucralose antibodies, they are well dispersed so as to not be detectable (if they are conjugated to a dye molecule) or may also be conjugated to another protein that can perform dye-activating chemistry when given the suitable substrate. This sample mixture now continues to flow into a third compartment that has several different areas (referred to as strips). There are preferably at least two strip areas to allow for a control and test area in this third compartment. In the test area, there will be an immobilized anti-sucralose antibody, which will bind to any anti-sucralose antibody-sucralose complexes, but not to any free anti-sucralose antibodies. The concentration of these complexes (in the case where sucralose is present in the sample solution) results in the appearance of a colored strip in the test region, either by concentration of the dye-labeled antibodies or by the ability to perform dye-generating chemistry due to the conjugation to a dye-generating enzyme. In the control area (which follows the test area), there is generally an immobilized antibody that is specific for another portion of the antibody, such that it will bind to the antibody in the absence of sucralose, resulting in the appearance of a colored strip in the control region under all conditions. This is an important component of the immunoassay is it ensures that the sample mixture has travelled through the entirety of the three compartments.

The main difference between the above scenario and that for the competition-based lateral flow immunoassay is that the solution encountered by the sample mixture contains sucralose bound to a dye or reporter molecule, not to an antibody. The third compartment contains the same materials, and in the same way for a plate-based competition assay (paragraph 0034), the presence of target analyte (sucralose) in the sample will prevent dye-labeled sucralose from binding to the test strip. Thus the appearance of color in the test region is indicative of a negative test for the target analyte.

The advantages of a lateral flow immunoassay are that there is no requirement for additional instrumentation for a positive test for the desired analyte. However, these tests tend to be semi-quantitative and have less sensitivity than instrument based methods.

The present invention also provides an ELISA assay kit for detecting sucralose in a sample, comprising a well plate containing a plurality of wells, wherein the wells are coated with a first plurality of the antibodies described herein. In one embodiment, the ELISA assay kit further comprises a solution necessary to perform a competitive ELISA, said solution comprises sucralose conjugated to a marker. In another embodiment, the ELISA assay kit further comprises a solution necessary to perform a sandwich ELISA, said solution comprises a second plurality of the above antibodies which are conjugated to a marker.

The present invention also provides a method for determining the concentration of sucralose in a sample, comprising the steps of: obtaining a sample; distributing the sample throughout a well plate, said well plate comprises wells that are coated with a plurality of the antibodies described herein; washing the well plate with a solution comprising sucralose conjugated to a marker, wherein said sucralose binds to any available antibodies in the wells; analyzing the well plate with a detector designed to detect the markers; and determining the concentration of sucralose in the sample using a concentration curve.

The present invention also provides a method for determining the concentration of sucralose in a sample, comprising the steps of: obtaining a sample; distributing the sample throughout a well plate, said well plate comprises wells that are coated with a first plurality of the antibodies described herein; washing the well plate with a solution comprising a second plurality of the above antibodies that are conjugated to a marker, wherein the second plurality of antibodies bind to sucralose that is already bound to the antibodies in the wells; analyzing the well plate with a detector designed to detect the markers; and determining the concentration of sucralose in the sample using a concentration curve.

REFERENCES

Beckman, Weiner and Davis, "Antibody Constructs in Cancer Therapy", Cancer, 109(2): 170-179, 2006.

Holliger and Hudson, "Engineered Antibody Fragments and the Rise of Single Domains", Nature Biotechnology, 23(9): 1126-1136, 2005.

Kabat, Wu, Perry, Gottesman, Foeller, "Sequences of Proteins of Immunological Interest", 5th Ed. Public Health Service, National institutes of Health, Bethesda, Md., 647-669, 1991.

Le Gall, Reusch, Little and Kipriyanov, "Effect of Linker Sequences Between the Antibody Variable Domains on the Formation, Stability and Biological Activity of a Bispecific Tandem Diabody", *Protein Engineering, Design & Selection,* 17(4):357-366, 2004.

Reffand Heard, "A Review of Modifications to Recombinant Antibodies: Attempt to Increase Efficacy in Oncology Applications", *Critical Reviews in Oncology Hematology,* 40:25-35, 2001

Reiter, Ulrich Brinkmann, Lee and Pastan, "Engineering Antibody Fv Fragements for Cancer Detection and Therapy: Disulfide-Stabilized Fv Fragments", Nature Biotechnology, 14:1239-1245, 1996.

Young, MacKenzie, Narang, Oomen and Baenziger, "Thermal Stabilization of a Single-Chain Fv Antibody Fragment by Introduction of a Disulphide Bond", FEBS Letters, 40 16396(377):135-139, 1995.

Zapata, Ridgway, Mordenti, Osaka, Wong, Bennett, Carter, "Engineering Linear F(Ab')2 Fragments For Efficient Production in *Escherichia Coli* and Enhanced Antiproliferative Activity", Protein Eng., 8(10):1057-1062, 1995.

What is claimed is:

1. An isolated polyclonal or monoclonal antibody that binds to sucralose.

2. The antibody of claim 1, wherein the antibody is produced by a hybridoma or by recombinant methods.

3. A host cell expressing the antibody of claim 1.

4. An immunoassay for detecting the presence of sucralose in a sample, comprising the steps of:
   a. contacting the sample with the antibody of claim 1, thereby forming immune complexes between the antibody and sucralose; and
   b. detecting and relating the binding of the antibody to the sucralose to the presence of the sucralose in the sample.

5. The immunoassay of claim 4, wherein the antibody is labeled.

6. An ELISA assay kit for detecting sucralose in a sample, comprising a well plate containing a plurality of wells, wherein the wells are coated with a first plurality of the antibodies of claim 1.

7. The ELISA assay kit of claim 6, further comprising a solution necessary to perform a competitive ELISA, said solution comprises sucralose conjugated to a marker.

8. The ELISA assay kit of claim 6, further comprising a solution necessary to perform a sandwich ELISA, said solution comprises a second plurality of the antibodies of claim 1 which are conjugated to a marker.

9. A method for determining the concentration of sucralose in a sample, comprising the steps of:
   a. obtaining a sample;
   b. distributing the sample throughout a well plate, said well plate comprises wells that are coated with a plurality of the antibodies of claim 1;
   c. washing the well plate with a solution comprising sucralose conjugated to a marker, wherein said sucralose binds to any available antibodies in the wells;
   d. analyzing the well plate with a detector designed to detect the markers; and
   e. determining the concentration of sucralose in the sample using a concentration curve.

10. A method for determining the concentration of sucralose in a sample, comprising the steps of:
   a. obtaining a sample;
   b. distributing the sample throughout a well plate, said well plate comprises wells that are coated with a first plurality of the antibodies of claim 1;
   c. washing the well plate with a solution comprising a second plurality of antibodies of claim 1 that are conjugated to a marker, wherein the second plurality of antibodies bind to sucralose that is already bound to the antibodies in the wells;
   d. analyzing the well plate with a detector designed to detect the markers; and
   e. determining the concentration of sucralose in the sample using a concentration curve.

* * * * *